United States Patent [19]

Jinotti

[11] Patent Number: 4,856,506
[45] Date of Patent: Aug. 15, 1989

[54] APPARATUS FOR MOUTH-TO-MOUTH RESUSCITATION

[76] Inventor: Walter J. Jinotti, 10 Scott St., New Brunswick, N.J. 08903

[21] Appl. No.: 297,326

[22] Filed: Jan. 17, 1989

Related U.S. Application Data

[63] Continuation-in-part of Ser. No. 142,443, Jan. 11, 1988.

[51] Int. Cl.⁴ ............................................. A61M 16/00
[52] U.S. Cl. ............................ 128/203.11; 128/207.16
[58] Field of Search ..................... 128/202.28, 202.29, 128/203.11, 207.16; 604/33, 249; 137/625.17, 625.42, 625.48

[56] References Cited

U.S. PATENT DOCUMENTS

| | | | |
|---|---|---|---|
| 374,402 | 12/1887 | Fell | 128/207.16 |
| 2,845,948 | 8/1958 | Parker | 137/625.17 |
| 3,242,921 | 3/1966 | Seeler | 128/203.11 |
| 3,407,810 | 10/1968 | Waldrep | 128/202.29 |
| 4,423,741 | 1/1984 | Levy | 137/625.48 |
| 4,648,868 | 3/1987 | Hardwick et al. | 137/625.17 |

*Primary Examiner*—Edgar S. Burr
*Assistant Examiner*—Aaron J. Lewis
*Attorney, Agent, or Firm*—Robert A. Green

[57] ABSTRACT

The apparatus includes a tube having a mouthpiece for a medical technician and a mouthpiece for insertion into the mouth of a patient.

Means in the tube provides a first flow path for air to flow from a patient into the tube and to the surrounding atmosphere, and a movable member in the tube is used to block the first flow path and provide a second flow path for air from the medical technician to the mouth of the patient.

11 Claims, 3 Drawing Sheets

APPARATUS FOR MOUTH-TO-MOUTH RESUSCITATION

CROSS-REFERENCE TO RELATED APPLICATIONS

This application is a continuation-in-part of application Ser. No. 07/142,443 filed Jan. 11, 1988.

BACKGROUND OF THE INVENTION

Mouth-to-mouth resuscitation has long been used in accident situations and the like to try to start breathing in a person who has stopped breathing. However, at the present time when the disease AIDS is a fearful menace and the disease can be transmitted through saliva, nurses, first aid squad members and other medical personnel may be reluctant to practice mouth-to-mouth resuscitation. Unfortunately, at the present time there is no simple, inexpensive, portable medically-safe apparatus for use in delivering mouth-to-mouth resuscitation.

This problem is solved by the present invention which comprises a simple, inexpensive mechanism which includes a simple valve arrangement in a device which can be inserted into the mouth of a patient and operated by a nurse without subjecting either one to the danger of receiving saliva from the other.

DESCRIPTION OF THE INVENTION

Figure 1:
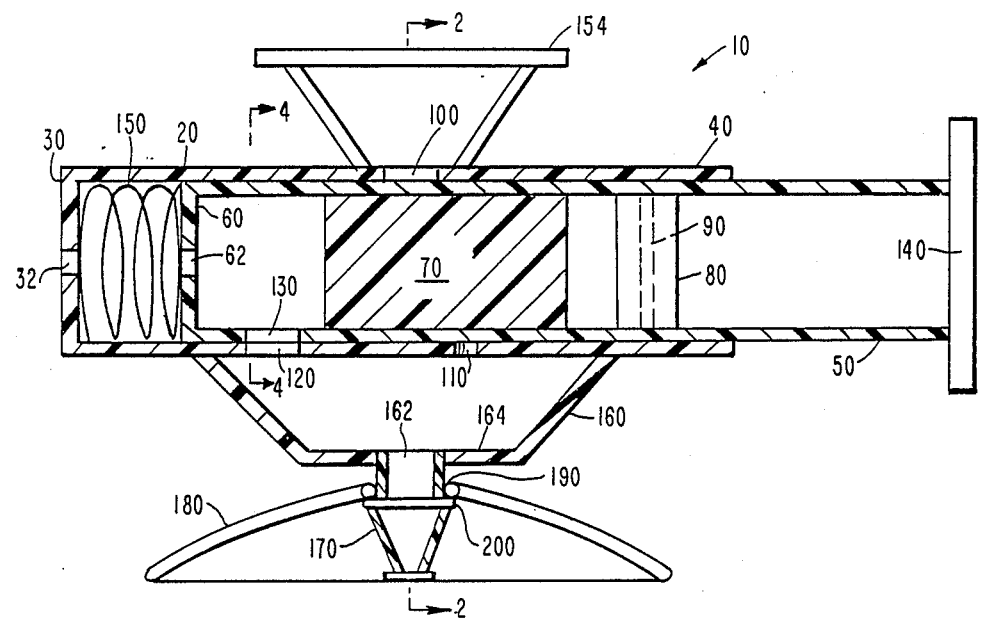
FIG. 1 is an elevational view, partly in section of apparatus embodying the invention.

The apparatus of the invention 10 comprises a plastic or metal tube 20 open at both ends 30 and 40 and having a plunger 50 slidably inserted in the right hand end 40 as seen in FIG. 1. End wall 30 has opening 62. The plunger 50 is of plastic or metal and is a tube which is open at the left end 60 and includes a solid plug portion 70 which occupies a portion of its length. To the right of the solid plug 70 is seated a rigid washer or disk insert 80 having a through-hole 90.

Figure 2:
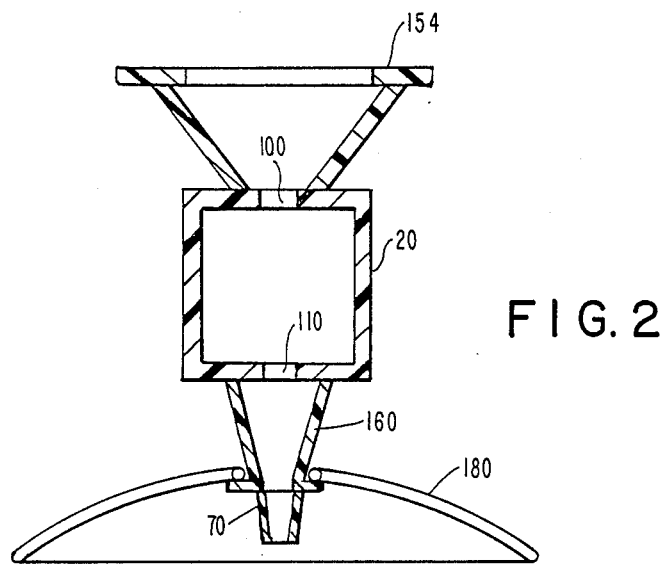
FIG. 2 is a sectional view along the lines 2—2 in FIG. 1.
Figure 4:
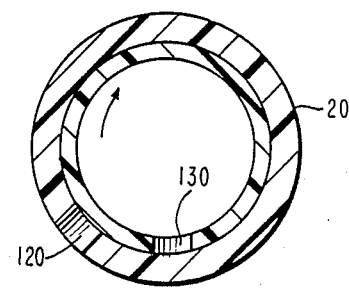
FIG. 4 is a sectional view along lines 4—4 in FIG. 1 and illustrating a modification in the method of operation of the invention.

Preferably, the tube 20 and plunger 50 have a square or rectangular cross-section as seen in FIG. 2 or a circular cross-section as seen in FIG. 4.

The tube 20 has two opposed aligned holes 100 and 110 in its wall and a third hole 120 in the wall adjacent to the left end of the plunger which also has a hole 130 in its wall in the vicinity of the hole 120. Holes 110 and 120 are in the same portion of the wall of the tube 20.

The plunger 50 has a finger-operable enlargement 140 at its outer free end and a helical spring 150 is provided between the end 60 of the plunger and the end wall 30 of the tube 20.

A tubular mouthpiece 154 for the user or operator, in the form of a truncated cone or the like, is secured to the tube 20 and aligned with and enclosing the hole 100 in the tube wall.

A patient mouthpiece 160, in the form of a truncated cone or the like and having a hole 162 in its small base 164, is secured to the all of the tube and overlaying and enclosing the two holes 110 and 120. The opposite end of this cone carries a short, small diameter mouthpiece tube 170 in hole 162 and a circular, flexible disk 180 used as a mask and having a central opening 190 has the tube 170 inserted in this central opening which is in somewhat air-tight engagement therewith. The opening in the mask or disk 180 engages a lip 200 on the mouthpiece tube 170. Cone 160 and tube 170 can be a single structure of any suitable shape.

In operation of the apparatus 10, the patient mouthpiece tube 170 is inserted into the mouth of a patient and the mask 180 is seated on the patient's face around the mouth. With the plunger 50 pushed to the left, the solid plug 70 closes off the aligned holes 100 and 110 and aligns the plug 80 and its through-hole 90 with the holes 100 and 110. Now the nurse can place her mouth on the open end of the tube 154 and can blow air into the mouthpiece and the air flows through the hole 100 in the tube 20, through the hole 90 in plug 80, and through the hole 110 in the tube 20 and into the mouth and lungs of the patient.

At the appropriate time, the plunger 50 is released and the spring 150 forces it to the right so that the solid plug 70 now blocks the aligned holes 100 and 110 and the aligned holes 120 and 130 now communicate with the patient mouthpiece 170. Now, air from the patient can flow through the holes 120 and 130 and out the open ends 62 and 32, respectively, of the plunger and tube 20 into the ambient air.

This cycle of operation is repeated as required.

Figure 3:
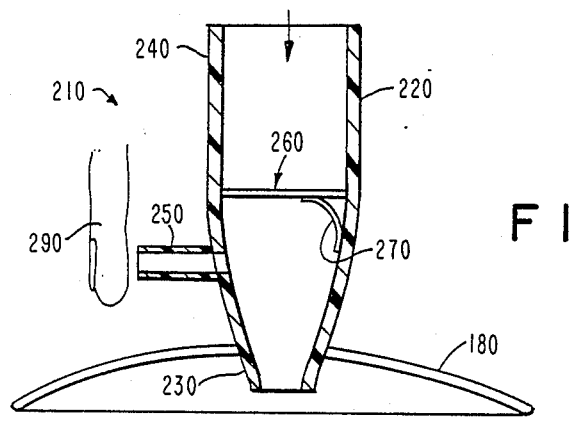
FIG. 3 is a sectional elevational view of a modification of the invention.

Another embodiment of the invention 210 illustrated in FIG. 3 includes a hollow open-ended tube 220 having one open end 230 constricted for insertion into the mouth of a patient and the opposite open end 240 which is adapted to be inserted into the mouth of a person administering mouth-to-mouth resuscitation.

Near the lower end 230 of the tube 220, a small diameter side tube 250 is secured in the wall of the tube 220. Above this side tube, a diaphragm or disk 260 of plastic or other preferably flexible material or the like, of the same diameter as the tube 220 is positioned within the tube across the long axis of the tube. The diaphragm is held in place by means of a leaf spring 270 suitably secured to the inner wall of tube 220 and to the lower surface of the diaphragm so that the diaphragm is held horizontal but is biased upwardly toward the user end of the tube. In its normal position, the diaphragm lies across the tube and prevents the flow of air along the tube from one end to the other.

A face mask 280 like the mask 180 is secured to the lower end of the tube 220.

In operation of this modification of the invention 210, the user places his finger 290 over the open end of the side tube 250 and thus blocks it; and with the end of the tube in the patient's mouth, the user blows air into the upper end 240 of the tube 220 and into the patient. The blown air causes the diaphragm 260 to bend downwardly and permits the flow of air to the patient. Then, the user's finger is removed from tube 250 when he stops blowing air, the diaphragm 160 returns to the horizontal position in which it blocks the tube 220 and air from the patient can flow out the side tube to ambient air. This cycle can be repeated as required.

The apparatus of the invention can be modified in structure or in usage to permit an operator to introduce air into a patient's lungs more than once before the air is permitted to be expelled from the patient.

In one arrangement, after an operator breathes air into a patient with holes 100, 90 and 110 aligned, the plunger is allowed to move to the right as seen in FIG. 1 and it is simultaneously rotated, to appropriate stops, so that holes 120 and 130 are out of alignment (FIG. 4). In this mode, the patient cannot exhale air.

Next, the plunger is again operated to permit the operator to breathe into the patient. Now, if desired, the plunger is allowed to move to the right and it is simultaneously rotated to appropriate stops to align the holes 120 and 130 and the patient can exhale air to the atmosphere through holes 120 and 130 and 31 and 32.

Figure 5:
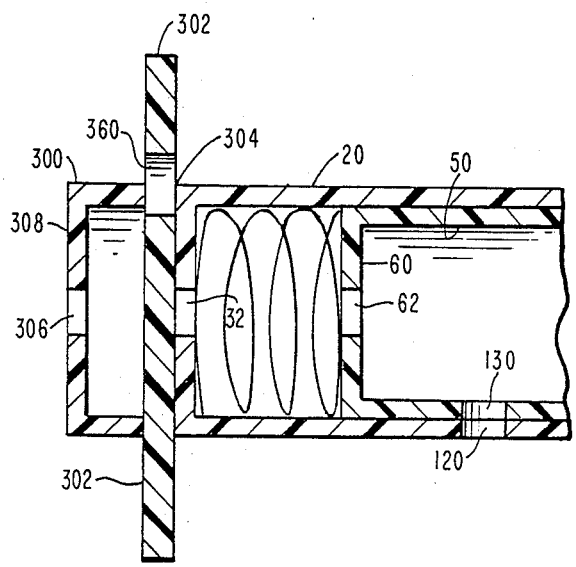
FIG. 5 is a side sectional view of a modification of the invention.

In one arrangement illustrated in FIG. 5, a tubular extension 300 is coupled to the open end of the tube 20 and a vertical slide 302 is inserted in a slot 304 in the tubular extension. The extension tube 300 has an opening 306 in its end wall 308. The slide 302 is solid except for a suitably sized opening 310 and it is slidable so that in one position, it can block the opening 32 in the open end 30 of the tube 20 and in a second raised or lowered position, its opening 360 can be aligned with the opening 32 in the end 30 of the tube and with the opening 62 in the end 60 of the plunger and the patient can expel air when the opening 120 and 130 are aligned.

Figure 6:
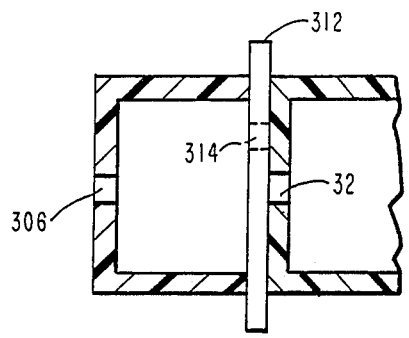
FIG. 6 is a side elevational view, in section, of a modification of a portion of the invention.
Figure 7:
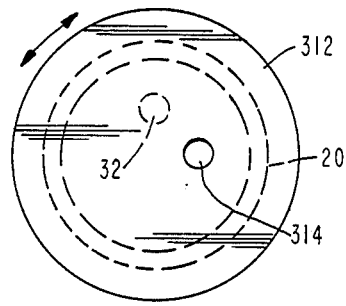
FIG. 7 is a front view of a portion of the apparatus of FIG. 6.

In another apparatus illustrated in FIGS. 6 and 7 a rotatable plate 312 is provided between extension tubes 300 and the end 30 of tube 20. The plate 312 has a small opening 314 and the plate can assume two positions in one of which it blocks the opening 32 in the open end of the tube 20 and in another of which its opening 314 is aligned with the opening 32 in the end 30 of the tube 20 and the patient can expel air when openings 120 and 130 are aligned.

Figure 8:
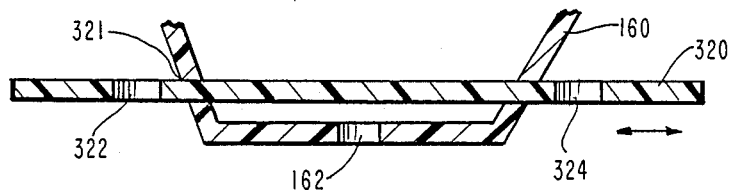
FIG. 8 is a sectional view of a modification of a portion of the invention.

If desired, as shown in FIG. 8, a horizontal slide plate 320 can be slidably inserted in a suitable slot 321 in the cone 160. The plate 320 is provided with spaced apart holes 322 and 324. In the orientation shown in FIG. 8, it is assumed that the plate 320 is in air-tight engagement with the cone 160 and the patient cannot expel air through hole 162. If the plate 320 is slid to the left or the right, one hole, 322 or 324, lies within the cone 160 and permits the patient to expel air through hole 162 and the hole 322 or 324 and the aligned holes 120 and 130.

What is claimed is:

1. Mouth-to-mouth resuscitation apparatus comprising
    a hollow, open-ended tube adapted to be disposed horizontally above the mouth of a patient to be resuscitated,
    said tube having a first end and a second end and first and second aligned opposed openings in its wall, the wall of said tube having a third opening close to said second end thereof,
    a plunger slidably disposed in said tube and having a first end extending out of said first end of said tube and having finger-operating means adjacent to said first end of said tube for sliding said plunger within said tube,
    said plunger having a second end disposed adjacent to said second end of said tube and having a vent opening in its wall near its second end, said finger-operating means sliding said vent opening in alignment with said third opening in the wall of said tube, said finger-operating means sliding said plunger within said tube thereby placing third opening out of alignment with said vent opening,
    a spring disposed in said tube between said second end of said plunger and said second end of said tube and urging said plunger away from said second end of said tube,
    a solid obstruction means in said plunger including a portion having a through hole which extends through said plunger transversely to the long axis thereof for aligning said through hold with said first and second aligned openings in said tube,
    the slidability of said plunger permitting it to occupy several positions in said tube in one of which said third opening in said wall of said tube is aligned with said vent opening in the wall of said plunger, in another of which said through hole is aligned with said opposed aligned first and second openings in said tube,
    an operator mouthpiece secured to said tube and aligned with said first opening in the wall of said tube, and
    a patient mouthpiece secured to said wall of said tube and aligned with said second opening in said wall of said tube,
    said operator mouthpiece in communication with said patient mouthpiece with said plunger being positioned with said through hole aligned with said first and second openings in said wall of said tube for directing air into the patient by the operator,
    said operator mouthpiece in communication with said patient mouthpiece with said plunger being positioned with said third opening and said vent opening in alignment for allowing the patient to vent air through the patient mouthpiece and through said aligned third opening and vent opening and through the open second end of said tube.

2. The apparatus defined in claim 1 and including a mask coupled to said tube and adapted to engage the face of the patient around the patient's mouth when the apparatus is in us.

3. The apparatus defined in claim 1 wherein said plunger is positioned whereby said first and second openings in the wall of said tube are accessible to said patient mouthpiece.

4. The apparatus defined in claim 1 and including a spring between said plunger and said second end of said tube to prevent movement of said plunger in said tube unless manual pressure is applied to said plunger by way of said finger-operable portion extending from said plunger.

5. The apparatus defined in claim 1 wherein said operator mouthpiece and said patient mouthpiece are both in the shape of truncated cones.

6. The apparatus defined in claim 1 wherein said patient mouthpiece is in the form of a truncated cone having a large base and a small base,
    the large base of said cone being secured to said tube overlying said second and third openings in the wall of said tube, and
    a small diameter mouthpiece secured to the small base of said cone,
    said mask being secured between said small diameter mouthpiece and said small base of said cone.

7. The apparatus defined in claim 1 and including a slidable plate positioned within said tube perpendicular to the longitudinal axis of said tube and adjacent to said second end of said tube and having a through hole, said slidable plate including means for sliding it in one position to block said open second end of said tube and in a second position to align the hole therein with the opening in said second end of said tube.

8. The apparatus defined in claim 1 wherein said plunger including said finger-operating means for rotating the plunger thereby positioning said third opening in said wall is out of communication with said vent opening in the wall of the plunger.

9. The apparatus defined in claim 1 and including a plate having a through hole and having means for rotating said plate, said plate being mounted adjacent to said second end of said tube, said plate being rotated into one position blocking the opening in said second end of said tube and in a second position having said through hole in communication with the opening in the second end of said tube.

10. The apparatus defined in claim 1 and including a slidable plate having a through hole and slidably positioned in the wall of said patient mouthpiece and parallel to the longitudinal axis of said plunger whereby in one position, said plate prevents the flow of air from the patient into the patient mouthpiece and in a second position, said through hole lies within the patient mouthpiece and permits air to flow from the patient into the patient mouthpiece.

11. Mouth-to-mouth resuscitation apparatus comprising a hollow, open-ended tube adapted to be disposed horizontally above the mouth of a patient to be resuscitated, said tube having a first end and a second end and first and second aligned opposed openings in its wall, the wall of said tube having a third opening close to said second end thereof, a plunger slidably disposed in said tube and having a first end extending out of said first end of said tube and having a finger-operating means adjacent to said first end of said tube for sliding said plunger within said tube, said plunger having a second end disposed adjacent to said second end of said tube and having a vent opening in its second end, said finger-operating means positioning said vent opening in alignment with said third opening in the wall of said tube, said finger-operating means sliding the plunger within said tube thereby placing the third opening out of alignment with said vent opening, a spring disposed in said tube between said second end of said plunger and said second end of said tube and urging said plunger away from said second end of said tube, a solid obstruction means in said plunger including a portion having a through hole which extends through said plunger transversely to the long axis thereof for aligning said through hole with said first and second aligned openings in said tube, the slidability of said plunger permitting it to occupy several positions in said tube in one of which the third opening in said wall of said tub is aligned with said vent opening in the wall of said plunger, in another of which said through hole is aligned with said opposed aligned first and second openings in said tube and in another of which none of said openings are aligned with each other, an operator mouthpiece secured to said tube and aligned with said first opening in the wall of said tube, and a patient mouthpiece secured to said wall of said tube and aligned with said second opening in said wall of said tube, said operator mouthpiece being in communication with said patient mouthpiece with said plunger being positioned with said through hole aligned with said first and second openings of said wall of said tube for directing air into the patient by the operator, said operator mouthpiece being out of communication with said patient mouthpiece with said plunger being positioned with said third opening and said vent opening in alignment whereby the patient vents air through the patient mouthpiece and through said aligned third opening and vent opening and through the open second end of said tube, said plunger being positioned so that neither said third opening nor said vent opening are aligned and said through hole is not aligned with said first and second openings.

* * * * *